US012661463B2

(12) United States Patent
Gardein et al.

(10) Patent No.: US 12,661,463 B2
(45) Date of Patent: Jun. 23, 2026

(54) GAS CONTROL DEVICE FOR A VENTILATOR

(71) Applicant: Loewenstein Medical Technology S.A., Luxembourg (LU)

(72) Inventors: Joachim Gardein, Icod de los Vinos (ES); Henry Hahn, Hamburg (DE); Benjamin Adametz, Hamburg (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 1318 days.

(21) Appl. No.: 17/257,916

(22) PCT Filed: Jul. 5, 2019

(86) PCT No.: PCT/DE2019/000186
§ 371 (c)(1),
(2) Date: Jan. 5, 2021

(87) PCT Pub. No.: WO2020/007389
PCT Pub. Date: Jan. 9, 2020

(65) Prior Publication Data
US 2021/0275763 A1 Sep. 9, 2021

(30) Foreign Application Priority Data

Jul. 6, 2018 (DE) ..................... 10 2018 005 341.6

(51) Int. Cl.
*A61M 16/00* (2006.01)
*A61M 16/20* (2006.01)
(52) U.S. Cl.
CPC ...... *A61M 16/022* (2017.08); *A61M 16/0066* (2013.01); *A61M 16/208* (2013.01); *A61M 2016/0027* (2013.01)

(58) Field of Classification Search
CPC .............. A61M 16/00; A61M 16/0066; A61M 16/0027; A61M 16/022;
(Continued)

(56) References Cited

U.S. PATENT DOCUMENTS 3,933,171 A * 1/1976 Hay .................... A61M 16/209
137/493
5,360,000 A * 11/1994 Carter ................. A61M 16/207
128/205.24
(Continued)

FOREIGN PATENT DOCUMENTS

CN 107308531 A 11/2017
DE 102008026321 A1 * 12/2008 ........ A61M 16/0858
(Continued)

OTHER PUBLICATIONS

DE-102008026321-A1 description translation accessed Oct. 18, 2023 (Year: 2023).*

*Primary Examiner* — Bradley H Philips
*Assistant Examiner* — Kira B Daher
(74) *Attorney, Agent, or Firm* — Abel Schillinger, LLP

(57) ABSTRACT

The present invention relates to a gas control device (10) for a ventilator, comprising a first gas channel (11) having a non-return valve (19), a second gas channel (12) and a switching apparatus (13), wherein the first gas channel (11) has an opening (14) for the outflow of gas with a seal (15) and a closure cap (16), wherein the switching apparatus (13) is configured to guide the gas stream of the first gas channel (11) past the non-return valve (19) in the event of a blockage/malfunction of the non-return valve (19). The present invention also relates to a ventilator comprising a gas control device (10) according to one of the above-mentioned features.

10 Claims, 6 Drawing Sheets

(58) Field of Classification Search
CPC .. A61M 2016/0033; A61M 2016/0039; A61M 2016/0042; A61M 16/20–22; A61M 2205/16; A61M 2205/3334; A61M 2205/3368
See application file for complete search history.

(56) References Cited

U.S. PATENT DOCUMENTS

| | | | | |
|---|---|---|---|---|
| 6,098,622 | A * | 8/2000 | Nobile | A61M 16/207 128/205.24 |
| 6,253,764 | B1 * | 7/2001 | Calluaud | A61M 16/202 128/205.24 |
| 7,066,177 | B2 * | 6/2006 | Pittaway | A61M 16/206 128/205.24 |
| 2013/0000637 | A1 | 1/2013 | Heesch | |
| 2013/0167843 | A1 * | 7/2013 | Kimm | A61M 16/209 128/205.24 |
| 2019/0151602 | A1 | 5/2019 | Tappehorn et al. | |
| 2019/0275283 | A1 | 9/2019 | Adametz et al. | |

FOREIGN PATENT DOCUMENTS

| | | | |
|---|---|---|---|
| DE | 202011102764 | U1 | 12/2011 |
| DE | 202017005964 | U1 | 12/2017 |
| EP | 3360595 | A1 | 8/2018 |
| EP | 3536369 | A1 | 9/2019 |
| WO | 2017059667 | A1 | 4/2017 |

* cited by examiner

GAS CONTROL DEVICE FOR A VENTILATOR

BACKGROUND OF THE INVENTION

1. Field of the Invention

The present invention relates to a gas control device for a ventilator, comprising a first gas channel with a non-return valve, a second gas channel, and a switching mechanism. The gas control device can be arranged in the ventilator or can be assigned to the ventilator.

2. Discussion of Background Information

Ventilators are used for treating respiratory disorders; the ventilators can be used in non-invasive and invasive ventilation, both in a hospital environment and outside of a hospital environment.

For ventilation of a patient, use can generally be made of a ventilator with an inspiratory branch for the respiratory gas flow and optionally with a branch for the expiratory respiratory gas flow. The branch for the expiratory respiratory gas flow permits the exhalation/expiration of a respiratory gas by the patient, while the branch for the inspiratory respiratory gas flow supplies the patient with respiratory gas.

In the ventilators known from the prior art, it can happen that blockages/disturbances occur in the expiratory branch of the ventilator.

If the inspiratory branch of the ventilator comprises a non-return valve, it is not possible for exhaled respiratory gas to return to the ventilator. Exhalation by the patient is then impeded.

It is therefore the object of the present invention to make available a device which ensures expiration of respiratory gas even in the event of a disturbance/blockage of a branch, in particular an expiratory branch, of a ventilator.

It is also the object of the present invention to make available a device which provides a gas channel that can be activated as and when required.

SUMMARY OF THE INVENTION

This object is achieved by a gas control device as per claim 1. Developments and advantageous embodiments are the subject matter of the dependent claims. Further advantages and features will become clear from the general description, and from the description of the illustrative embodiments.

The present invention relates to a gas control device for a ventilator, comprising a first gas channel with a first valve, wherein the first gas channel and the valve are configured to permit the passage of a pressurized gas stream in a first direction and to block a pressurized gas stream in a second direction, wherein an opening branches off from the first gas channel and leads to a bypass channel, for the valve, wherein a second valve is configured to block and/or at least temporarily permit a gas stream from the first gas channel to the bypass channel, wherein a switching mechanism is configured to control the second valve to block and/or at least temporarily permit a gas stream from the first gas channel to the bypass channel.

The present invention also relates to a gas control device comprising a first gas channel with a first valve, wherein the first gas channel and the valve are configured to permit the passage of a pressurized gas stream in a first direction and to block a pressurized gas stream in a second direction, wherein an opening branches off from the first gas channel and leads to a bypass channel, for the valve, wherein a second valve is configured to block and/or at least temporarily permit a gas stream from the first gas channel to the bypass channel, wherein a switching mechanism is configured to control the second valve to block and/or at least temporarily permit a gas stream from the first gas channel to the bypass channel.

The present invention is also characterized in that the second direction is counter to the first direction.

The present invention is also characterized in that the first valve is a pneumatically actuated non-return valve, which is actuated by the force of the pressurized gas stream in the second direction, and therefore the gas stream cannot pass through the non-return valve in a second direction.

The present invention is also characterized in that the gas stream of the second direction is respiratory gas of expiration, and the gas stream of the first direction is respiratory gas of inspiration.

The present invention is also characterized in that a respiratory gas source suctions respiratory gas from the environment and conveys it along the first gas channel for inspiration in the first direction to the tube port and the breathing tube, wherein the gas stream passes through the opened non-return valve.

The present invention is also characterized in that the switching mechanism opens the valve, and therefore the pressurized gas stream of expiration passes at least in part through the opening and through the bypass channel into the environment.

The present invention is also characterized in that the valve is configured as a pneumatic valve, wherein a seal of the valve closes or opens the gas-conveying connection between opening and bypass channel, and wherein a second gas channel is configured to conduct a pneumatic control pressure onto the surface of the seal.

The present invention is also characterized in that the seal charged with the control pressure is configured to bear sealingly on the edge of the opening and thus prevent a gas stream from the opening into the bypass channel.

The present invention is also characterized in that the second gas channel is connected pneumatically to the breathing tube or the gas channel, and the switching mechanism at least temporarily opens or closes the pneumatic connection.

The present invention also relates to a gas control device for a ventilator, comprising a first gas channel with a non-return valve, a second gas channel, and a switching mechanism, wherein the first gas channel has an opening for the outflow of gas with a seal and a closure cap.

According to the invention, the gas control device is configured to guide the gas stream of the first gas channel past the non-return valve in the event of a blockage/disturbance of an expiratory branch of the ventilator. In this way, exhalation by the patient is ensured in the event of a blockage/disturbance of the expiratory branch. For example, the first gas channel is connected to the second gas channel. A separate design of the first gas channel and of the second gas channel, wherein the second gas channel is fed through a separate gas channel, is conceivable in an alternative embodiment. It is also conceivable to use the gas control device according to the invention likewise in the event of a blockage/disturbance in an inspiratory branch of the ventilator. In such a case, the gas control device could be used to ensure inhalation by a patient in the event of a blockage/disturbance in the inspiratory branch of the ventilator.

The gas control device is configured to control the second gas channel, in the event of a blockage or disturbance of the expiratory branch, in such a way that the gas stream of the first gas channel flows out via the opening or flows past the non-return valve via a bypass channel. The gas stream of the first gas channel is here generally composed of an inhalation gas and/or an exhalation gas. Particularly in the event of a blockage/disturbance of the expiratory branch, the exhalation gas of the patient can be returned via the inspiratory branch/the first gas channel as far as the non-return valve. Therefore, the opening of the first gas channel is advantageously arranged in the region of the non-return valve, downstream from the non-return valve in the inspiration flow direction.

The gas control device is configured to control the pressure in the second gas channel. Here, control can mean that the switching mechanism can be configured to free or block the second gas channel. In an alternative embodiment, the switching mechanism can be continuously controllable in a stepless manner. Based on the control of the gas stream of the second gas channel, in particular the freeing or blocking of the second gas channel, the gas stream of the first gas channel (the exhalation gas/the exhalation gas stream) can be guided past the non-return valve. The gas stream of the first gas channel is guided past the non-return valve via a bypass channel. The gas stream diverted into the bypass channel can be delivered again to the first gas channel, advantageously in a region lying upstream from the non-return valve in the inspiration flow direction of the gas stream, or can be carried off via the bypass channel or a separate branch, which can be configured as an inspiratory or expiratory branch.

The gas control device can be configured to be controllable on the basis of a detected volume, a detected flow rate or a detected pressure of a gas stream.

In particular, the gas control device can comprise at least one sensor, wherein the switching mechanism can be configured to be controllable on the basis of a parameter detected by the at least one sensor.

The at least one sensor of the gas control device, for example as part of the switching mechanism, can be configured to detect at least one respiration parameter, respiratory gas parameter and/or another parameter from output signals. One or more detected parameters can here form a function relating, for example, to measurements of one or more of the following: (peak) flow, flow rate, (tidal) volume, pressure, temperature, humidity, speed, acceleration, gas composition (e.g. concentration(s) of one or more constituents), thermal energy dissipation, (intentional) gas leakage and/or other measurements relating to the respiratory gas flow.

Respiration parameters can be derived, for example, from gas parameters and/or other output signals, wherein one or more respiration parameters can be one or more of the following: respiration frequency, respiration duration, inhalation time or duration, exhalation time or period, shape of the respiratory flow curve, transition time from inhalation to exhalation and/or vice versa, transition time from (peak) inhalation flow rate to (peak) expiration flow rate and/or vice versa, shape of respiration pressure curves, maximum proximal pressure drop (per respiration cycle and/or phase), fraction of inhaled oxygen, and/or other respiration parameters.

The gas control device according to the invention enables a patient to exhale even in the event of a blockage/disturbance of the expiratory branch of the ventilator.

The gas control device is configured, for example via the switching mechanism, to control the gas stream of the second gas channel and to allow the gas stream of the first gas channel to be guided past and around the non-return valve through the opening. By the control of the gas stream of the second gas channel, the opening on which the seal lies, which is sealed off by the gas stream/pressure of the second gas channel, can be opened. The gas stream of the first gas channel can emerge from the opening. In the event of a blockage of the second gas channel, the pressure ratio in the region of the seal changes, such that a gas pressure of the gas stream of the first gas channel is greater than a gas pressure of the second gas channel. Generally, the gas pressure of the blocked second gas channel equals zero.

The bypass channel is generally formed in a ring shape around the opening of the first gas channel. In a ring shape can also mean enclosing the opening. The ring shape affords the advantage that gas can flow out of the opening at an angle of up to 360°. In this way, a correspondingly large amount of expiratory exhalation gas can be carried away simultaneously via the opening of the first gas channel. The bypass channel is advantageously configured to focus the gas stream delivered via the opening and to carry it off in one direction.

In one embodiment, the gas control device is configured, for example via the switching mechanism, to free or block the second gas channel. For example, the switching mechanism is configured to free the second gas channel, as a result of which the seal, which lies on the opening, can be subjected to a gas stream/pressure. By charging the seal with a gas stream/pressure, the seal can be pressed onto the opening. The switching mechanism can also be configured to block the second gas channel, such that the seal, which lies on the opening, cannot be subjected to a gas stream/pressure. In this case, the seal lies loosely on the opening. In this embodiment, a gas stream of the first gas channel can flow into a bypass channel through the seal lying loosely on the opening.

Advantageously, the gas control device is configured, for example via the switching mechanism, to block the second gas channel in the event of a blockage/disturbance of the expiratory branch. To block means that the switching mechanism does not provide a gas stream/pressure in the second gas channel or closes the latter. By virtue of the seal not being subjected to a gas stream of the second gas channel, the gas stream of the first gas channel is sufficient to lift the seal and to transfer the gas stream from the first gas channel into the bypass channel.

The gas control device is typically configured, for example via the switching mechanism, to free the second gas channel during a use of the ventilator in a valve system, such that the second gas channel can guide a gas stream. During the use in a valve system, the expiratory and/or the inspiratory branch of the ventilator are/is free of disturbance, and the opening of the gas control device is closed by a pressure of the second gas channel, which is generally designed as a pressure channel.

To free means that the gas control device, for example via the switching mechanism, opens the second gas channel for the passage of a gas stream, and therefore the seal, which lies on the opening, is subjected to a gas stream/pressure. Generally, the gas stream of the second gas channel is subjected to a pressure of 1 mbar to 100 mbar. By means of the pressure, the seal is pressed onto the opening and sealed off.

During normal operation of the ventilator, the gas control device is configured to seal off the seal the gas stream from the first gas channel by means of the gas stream of the second gas channel, which is conveyed to the seal of the gas control device via a connector piece of the closure cap.

Thus, during normal operation/use in a valve hose system, the function of the non-return valve can be maintained.

In a disturbance-free operating state of the ventilator, for example with a disturbance-free expiratory branch, the gas control device is configured to apply a pressure to the sealing membrane via the second gas channel and thereby close the opening of the gas control device.

In the event of a blockage/disturbance of the expiratory branch, the gas control device is configured to block the second gas channel. In this way, there is no pressure on the sealing membrane, and the opening can be opened by a gas pressure of the gas stream of the first gas channel. The gas stream emerging via the opening can be delivered again to the first gas channel or can be carried away via a separate branch.

In one embodiment, the switching mechanism (as part of the gas control device) can be configured to be controllable on the basis of a time-controlled switching of an expiration and/or an inspiration.

In an alternative embodiment, the switching mechanism (as part of the gas control device) can be configured to be controllable on the basis of a parameter of the first gas channel. For example, at least one parameter of the gas stream in the first gas channel can be detected by means of a sensor. For example, a pressure inside the first gas channel can be detected by means of a pressure sensor. The switching mechanism is then configured to be controllable depending on the detected pressure of the gas stream in the first gas channel. For example, in the alternative embodiment, the switching mechanism can be configured to free or block the second gas channel depending on whether a predetermined threshold value is reached. Such a threshold value can be, for example, a value lying above the average detected pressure in the first gas channel. If the threshold value is exceeded, the switching mechanism can be configured to block the second gas channel. If the pressure in the first gas channel drops below the threshold value, the switching mechanism can free the second gas channel.

In a further alternative embodiment, the flow rate or a volume of the gas stream of the first gas channel can also be detected for example by means of a sensor. The switching mechanism can be configured to be controllable on the basis of the detected flow rate or the detected volume of the gas stream. The switching mechanism can also be configured to be controllable on the basis of further parameters of the gas stream of the first gas channel.

In a further alternative embodiment, the switching mechanism (as part of the gas control device) can also be configured to be variably switchable, wherein the switching mechanism can be configured to steplessly control a pressure of the gas stream in the second gas channel between 0 mbar and 1 bar, in particular between 0 mbar and 100 mbar. The switching mechanism can also be configured to increase the gas stream/pressure in the second gas channel to a predetermined value continuously over a predetermined period of time.

The seal for a part of the gas control device, in particular for a valve, is designed to allow the gas stream of the first gas channel to flow through the opening in the event of a blocked second gas channel. The seal seals off the bypass channel from the opening. The seal advantageously has a shape which places and holds the seal on the opening in a gas-free state of the first and second gas channel. The seal has a contact surface ratio of between 4/5 and 2/3. The seal is dimensioned in such a way that it can be lifted by a gas stream of the first gas channel when the seal is not subjected to a gas stream/pressure by a gas stream of the second gas channel. Moreover, the seal generally comprises a peripheral, reinforced edge, which is configured to bear on the edge of the bypass channel. The peripheral, reinforced edge can have a latching structure or holding structure, which makes it easier to hold the seal on the edge of the bypass channel. For example, the peripheral, reinforced edge can have a border that is designed to bear on an elevation of the edge of the bypass channel.

In one embodiment, the seal is arranged lying on the opening and comprises a weight. The weight, which is preferably integrated into the seal, assists in the positioning of the seal on the opening. Generally, in the region in which the weight is formed integrally, the seal has a greater material thickness than in the surrounding regions of the seal. The seal is typically circular. The seal can alternatively be rectangular, square or oval or can have another geometric shape. Generally, the seal is designed corresponding to the shape of the opening and/or to the shape of the bypass channel surrounding the opening. Between the edge of the bypass channel and the weight, the seal can form a bulge, which faces in the direction of the first gas channel and prevents slipping of the seal.

In a development of the invention, the weight is designed in a ring shape in the middle of the seal. Here, in the middle means in the center of the circular seal. Generally, the ring-shaped weight is designed in the form of a plain washer. However, the weight can likewise have a rectangular or oval shape. By virtue of the ring shape, the seal can be placed onto an edge of the opening extending peripherally around the opening. The seal can also bear only in some parts on the edge of the opening. Generally, the shape of the weight corresponds to the shape of the opening or to the shape of the edge of the opening. The weight places a load on the seal, as a result of which the seal lies loosely on the edge of the opening. Optionally, the weight can be rectangular or have another geometric shape. Moreover, the weight can be arranged in another region of the seal.

The seal is made of an elastomeric material, and the weight is made of a metal. The seal is generally made of an elastomeric material having a hardness in the range between 15 and 25 Shore A, in particular between 18 and 22 Shore A. For example, the seal is produced from a silicone. Alternatively, the weight can be made of another material, for example a hard plastic or a combination of metal and plastic.

In a further development of the invention, the seal has an embossing, which is formed in the region of the weight, facing in the direction of the first gas channel. The embossing can be designed as a conical elevation, the tip of which extends pointing from the opening into the first gas channel. For example, the embossing can be formed in the recess of the weight, which recess is provided by the washer-like design. The embossing helps hold the seal on the opening of the first gas channel. The embossing can optionally be designed in any desired shape that holds the seal in its position on the opening. In an alternative embodiment, the seal can be designed without embossing.

In an advantageous development of the invention, the closure cap is configured to be placeable onto the opening. Generally, the closure cap can be clipped onto the opening. This affords the advantage that the closure cap, when placed onto the seal lying on the opening, does not change the position thereof. To be able to be clipped onto the opening, the closure cap generally has at least two extensions, which typically have barbs that engage in recesses formed at an outer region of the opening. Alternatively, the closure cap of the gas control device can be provided with a bayonet catch. Optionally, the closure cap can be secured on the opening by alternative latching elements.

In a further advantageous development of the invention, the closure cap comprises a connector piece which is connectable to the second gas channel. The shape of the connector piece generally corresponds to the shape of the second gas channel. Alternatively, the connector piece and the gas channel are connectable by an adapter. The connector piece is configured to conduct the gas stream/pressure of the second gas channel to the seal. The connector piece is generally connected to the closure cap. The connector piece is typically connected to the closure cap in such a way that a gas stream can be applied vertically and centrally to the seal. Alternatively, the connector piece can also be arranged laterally on the closure cap. The connector piece, which can likewise be designed as a channel, has a diameter of between 0.1 mm and 0.5 mm, for example.

According to the invention, during normal operation of the ventilator, the switching mechanism (as part of the gas control device) is configured to free the second gas channel and convey a gas stream/pressure via the second gas channel and the connector piece to the seal and close the opening. During normal operation of the ventilator, there is no disturbance/blockage of an expiratory or inspiratory branch of the ventilator. The switching mechanism is configured to control the gas stream/pressure of the second gas channel. Generally, the gas stream in the second gas channel is subjected to a gas stream/pressure of 1 mbar to 1 bar, in particular of between 10 mbar and 150 mbar. In this way, the seal is sealed onto the opening of the first gas channel, such that the gas stream of the first gas channel cannot escape via the opening.

According to the invention, in the event of a blockage/disturbance of the expiratory branch, the switching mechanism (as part of the gas control device) is configured to block the second gas channel. Through the blocking of the second gas channel, the gas stream/pressure of the second gas channel comes to a standstill. The gas control device can lead the gas stream of the first gas channel out via the opening. In the event of the second channel being blocked by the switching mechanism, the gas stream/pressure in the first gas channel is greater than in the second gas channel. In this way, the gas stream of the first gas channel can lift the seal, which lies on the opening, and can lead the gas stream into the bypass channel and bypass the non-return valve. The seal is lifted in such a way that the seal, in the region of the boundary of the seal, is pressed/held by the closure cap onto the edge of the bypass channel. As soon as the second gas channel is blocked and there is no longer any gas stream/pressure applied to the seal, the weight of the seal is lifted by the gas stream of the first gas channel, such that the seal lying on the edge of the opening is lifted, as a result of which the gas stream can flow from the first gas channel into the bypass channel via the opening.

The present invention moreover also comprises a seal for a part of the gas control device for a ventilator, comprising a first gas channel with a non-return valve, a second gas channel, and a switching mechanism, wherein the first gas channel has an opening for the outflow of gas, with a seal and a closure cap.

According to the invention, the seal has a weight and, in the event of a blocked second gas channel, is configured to allow a gas stream of the first gas channel to flow through the opening. The seal is generally circular. Alternatively, however, the seal can also be rectangular or can have another geometric shape. The seal is typically made of an elastomeric material, for example silicone. The seal generally has a hardness in the range between 15 and 25 Shore A, in particular between 18 and 22 Shore A. In an alternative embodiment, the weight can be formed in another region of the seal.

In one embodiment, the seal has an at least partially peripheral edge which is configured to engage in a recess of the gas control device. The peripheral edge is preferably reinforced and can have an embossing that engages in a recess at the edge of the bypass channel. The peripheral edge of the seal serves, on the one hand, for sealing purposes and, on the other hand, for positioning the seal on the edge of the bypass channel. It is pressed/held/sealed onto the edge of the bypass channel by the closure cap. The edge of the bypass channel can have an elevation which is configured to bear on the seal in such a way that a border of the seal comes into engagement with the elevation.

The present invention also relates to a gas control device, which gas control device is designed as an electrical and/or pneumatic control unit in a ventilator and is configured to permit the passage of a pressurized gas stream in a first direction and to block a pressurized gas stream in a second direction and to block and/or at least temporarily permit a gas stream from the first gas channel to the bypass channel, wherein the gas control device is configured to block and/or at least temporarily permit a gas stream from the first gas channel to the bypass channel.

The gas control device can be designed as an electrical and/or pneumatic control unit which comprises various actuators and sensors, for example at least the switching mechanisms, valves and the gas source, and controls these in a coordinated manner within the meaning of the invention.

The gas control device can be designed as an electrical and/or pneumatic control unit and is configured to permit the passage of a pressurized gas stream in a first direction and to block a pressurized gas stream in a second direction and to block and/or at least temporarily permit a gas stream from the first gas channel to the bypass channel, wherein a gas control device (10) is configured to block and/or at least temporarily permit a gas stream from the first gas channel to the bypass channel.

The present invention moreover comprises a closure cap for a gas control device for a ventilator, comprising a first gas channel with a non-return valve, a second gas channel, and a switching mechanism, wherein the first gas channel has an opening for the outflow of gas, with a seal and a closure cap.

According to the invention, the closure cap, at least in some parts, has extensions which form barbs and which are configured to engage in recesses on the gas control device. Alternatively, the closure cap can comprise a bayonet catch which is configured to engage in recesses on the opening.

The present invention further comprises a ventilator comprising a gas control device as per at least one of the aforementioned features.

Within the context of the invention, gas can be any breathable gas or gas mixture. In particular air, oxygen, respiratory gas of expiration or expiratory gas of inspiration.

BRIEF DESCRIPTION OF THE DRAWINGS

Preferred illustrative embodiments of the invention are explained in more detail below with reference to highly simplified, schematic illustrations, in which.

In the figures, the same structural elements each have the same reference numbers.

DETAILED DESCRIPTION OF EMBODIMENTS OF THE INVENTION

Figure 1A:
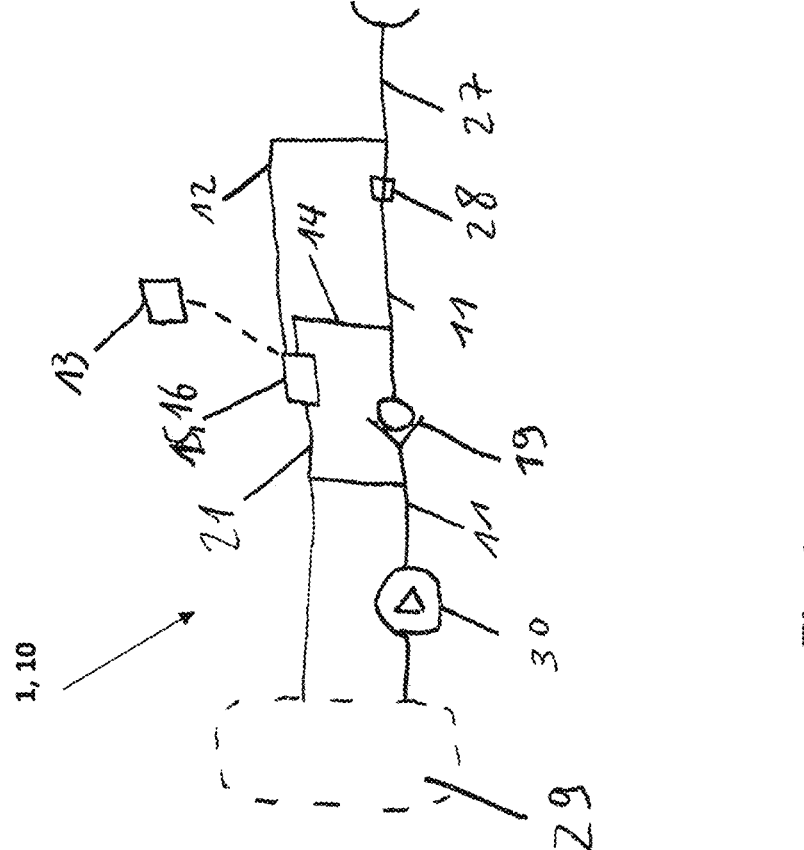
FIG. 1a shows a schematic view of a gas control device according to the invention.

FIG. 1a shows a schematic view of a gas control device 10 according to the invention for a ventilator 1. Ventilators 1 generally have an inspiratory branch, which is provided for delivering respiratory gas to a patient, and an expiratory branch, which serves to carry away respiratory gas that has been exhaled by the patient. The gas control device (10) can be designed as an electrical and/or pneumatic control unit and can be configured to permit the passage of a pressurized gas stream in a first direction and to block a pressurized gas stream in a second direction and to block and/or at least temporarily permit a gas stream from the first gas channel (11) to the bypass channel (21), wherein a gas control device (10) is configured to block and/or at least temporarily permit a gas stream from the first gas channel 11 to the bypass channel (21).

The gas control device 10 according to the invention, shown in FIG. 1a, is provided for use in a ventilator 1 or as part of a ventilator and has a first gas channel 11 with a first valve (19), wherein the first gas channel (11) and the valve (19) are configured to permit the passage of a pressurized gas stream in a first direction and to block a pressurized gas stream in a second direction, wherein an opening (14) branches off from the first gas channel 11 and leads to a bypass channel (21), for the valve (19), wherein a second valve (15, 16) is configured to block and/or at least temporarily permit a gas stream from the first gas channel (11) to the bypass channel (21), wherein a switching mechanism (13) is configured to control the second valve (15, 16) to block and/or at least temporarily permit a gas stream from the first gas channel 11 to the bypass channel (21).

The switching mechanism here comprises, for example, the valve block 13 with the first valve 19 and second valve, the first gas path 11 and second gas path and the bypass 14, 21. Optionally, the switching mechanism 13 also comprises the pneumatic or electronic control for the components of the valve block.

A gas source or respiratory gas source 30, for example a blower, conveys gas or respiratory gas, suctioned for example from the environment 29, along the first gas channel (11) for inspiration in the first direction (25) to the tube port (28) and the breathing tube (27). The gas stream passes through the opened non-return valve (19).

An expiration by the patient ensures a stream of respiratory gas in a second direction through the breathing tube, the port (28) and the first gas channel (11) as far as the non-return valve (19). The latter is a pneumatically actuated non-return valve (19) which is actuated by the force of the pressurized gas stream of expiration, in the second direction, and therefore cannot pass through the non-return valve (19). Since the opening (14) is connected to the first gas channel (11), the pressurized gas stream of expiration also spreads, in the second direction, into the opening and reaches as far as the valve (15, 16). Provided that the switching mechanism (13) opens the valve (15, 16), the pressurized gas stream of expiration flows further along the opening and the bypass channel (21) into the environment (29) or alternatively into the first gas channel and from there at least in part into the environment.

The valve (15, 16) can be designed as a pneumatic valve. In this case, a seal (15) of the valve can close or open the gas-conveying connection between opening 14 and bypass channel. The control impulse for the seal (15) of the valve comes from a second gas channel (12), which conducts a pneumatic control pressure to the surface of the seal 15. When the control pressure is applied to the seal, the latter bears sealingly on the edge 22 of the opening 14 and thus prevents a gas stream from the opening into the bypass channel.

The second gas channel can for this purpose be fed pneumatically from the breathing tube or the gas channel (11). Another compressed gas source, for example a control blower, is likewise conceivable. The switching mechanism 13 at least temporarily opens or closes the pneumatic connection between the second gas channel 12 and the breathing tube or the gas channel (11).

The valve (15, 16) can be designed as a switching valve. In this case, an activation of the valve, by the switching mechanism 13, opens or closes the gas stream from the opening 14 into the bypass channel. In this case, a second gas channel is not needed.

Ventilators generally have an inspiratory branch, which is provided for delivering respiratory gas to a patient, and an expiratory branch, which serves to carry away respiratory gas that has been exhaled by the patient.

Figure 1B:
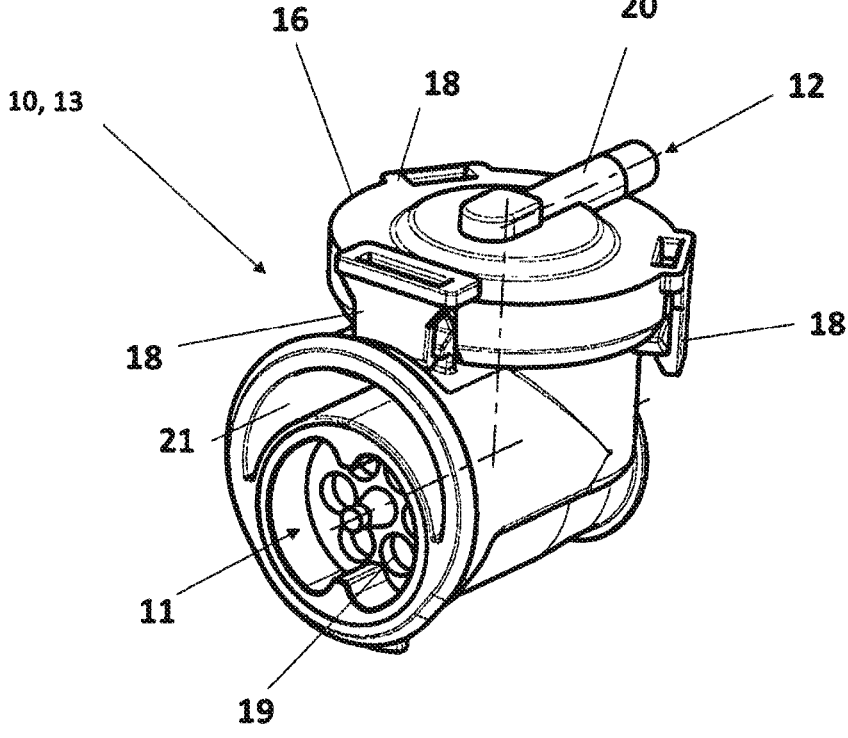
FIG. 1b shows a schematic view of a gas control device according to the invention, wherein the gas control device is only partially illustrated here, namely as a switching mechanism or as a valve block.

FIG. 1b shows a schematic view of a gas control device 10 according to the invention for a ventilator. The gas control device (10) is shown here only in part, namely as a switching mechanism 13 or as a valve block, and comprises a first gas channel (11) with a first valve (19), wherein the first gas channel (11) and the valve (19) are configured to permit the passage of a pressurized gas in a first direction and to block a pressurized gas in a second direction, wherein an opening (14) branches off from the first gas channel 11 and leads to a bypass channel (21), for the valve (19), and a second valve (15, 16) for opening or closing the bypass channel (21).

The gas control device 10 according to the invention shown in FIGS. 1 and 1b is provided for use in a ventilator and has a first gas channel 11 (inspiratory branch) which conveys a gas stream in the direction of a patient. The first gas channel 11 comprises a non-return valve 19 and an opening (not shown) with a seal (not shown). The opening and the seal are concealed by a closure cap 16 in FIG. 1. The non-return valve 19 prevents return of a respiratory gas/gas stream that comes from the patient and that has been contaminated by the exhalation.

Moreover, the gas control device 10 has a second gas channel 12, which conveys a gas stream to the opening (not shown). The second gas channel 12 is connected to by a connector piece 20 to the closure cap 16, which is clipped onto the opening of the first gas channel. The second gas channel 12 extends via the connector piece 20 to the closure cap 16 and is controlled by a switching mechanism (not shown). A gas stream can flow through the second gas channel 12.

The switching mechanism (not shown) can free or block the second gas channel 12. The switching mechanism here frees the second gas channel 12 for a gas stream or a gas pressure or a gas stream volume. During normal operation of the ventilator, the second gas channel 12 is freed, such that the gas stream or pressure can be guided via the connector piece 20 to the seal (not shown) inside the closure cap 16. By means of the gas stream/pressure of the second gas channel 12, the seal is pressed completely onto the opening, and the opening is thus closed. In this way, during normal operation of the ventilator in which there is no blockage, an outward flow of an inspiratory gas stream of the first gas channel 11, which is intended to be conveyed to the patient, via the opening into the bypass channel 21 is prevented. This is not necessary in this case, since the expiratory branch is blockage-free, and therefore the respiratory gas exhaled by the patient can be discharged via the expiratory branch.

By contrast, in the event of a blockage/disturbance of an expiratory branch of the ventilator, exhalation by the patient is prevented or made difficult. Moreover, by means of the non-return valve 19, the patient cannot exhale via the inspiratory branch. In the event of a blockage/disturbance of the expiratory branch of the ventilator, the switching mechanism blocks the second gas channel 12. By means of the blocked gas channel 12, the gas stream of the second gas channel 12 acting on the seal comes to a standstill, as a result of which the gas stream of the first gas channel 11 can lift the seal lying on the opening, such that the gas stream of the first gas channel is guided via a bypass channel 21 around the non-return valve. In this case, the gas stream or pressure of the first gas channel 11 is therefore greater than the gas stream or the pressure of the second gas channel 12, as a result of which the gas stream of the first gas channel 11 is able to lift the seal lying on the opening. The seal is dimensioned and designed in such a way that that the gas stream of the first gas channel 11 can lift it when the gas channel 12 is blocked. Here, lift means that the seal is held peripherally at its peripheral edge by the closure cap 16 on the edge of the bypass channel 21 and is pressed upward in the direction of the center of the circular seal by the gas stream of the first gas channel 11. The weight of the seal is proportioned in such a way that it deposits the seal automatically onto the opening when the gas stream of the second gas channel 12 subsides.

The patient can thus exhale even in the event of a blockage/disturbance of the expiratory branch.

In a leakage system, the switching mechanism blocks the second gas channel or does not apply pressure to the seal. In this case, the switching valve is configured to continuously permit an outflow of gas.

In a valve system, the switching mechanism is configured to switch in accordance with the time-controlled expiration of the ventilator. Thus, when the ventilator is switched to expiration, the switching mechanism is configured to block the second gas channel 12. The expiration by a patient is ensured in this way, since the opening of the gas control device is opened during the expiration and a return flow of gas can escape via the opening.

During normal operation of the expiratory branch of the ventilator, the switching mechanism switches the second gas channel 12 free, as a result of which a gas stream can flow into the second gas channel 12 and is subjected to a pressure. By means of the gas stream in the second gas channel 12, the seal is sealed on the opening, as a result of which an outflow of inspiratory gas through the opening is prevented during the normal operation.

In the present embodiment, the closure cap 16 comprises three extensions 18, by means of which the closure cap 16 can be clipped onto the opening of the first gas channel 11. Moreover, a connector piece 20 is formed on the closure cap, and the second gas channel 12 can be connected thereto. The connector piece 20 is arranged centrally on the closure cap 16, such that the gas stream/pressure can be applied centrally and uniformly to the seal via the connector piece 20 and the closure cap 16.

Thus, during normal operation, the gas control device 10 shown in FIG. 1*b* is configured to guide the gas stream in the first gas channel 11 through the non-return valve 19 to the patient. During normal operation of the expiratory branch, the opening of the first gas channel 11 is closed, and the function of the non-return valve 19 is maintained. In the event of a blockage/disturbance of the non-return valve 19, the gas control device 10 bypasses the non-return valve 19.

The switching mechanism (not shown) of the gas control device 10 is triggered by the time-controlled switching of the ventilator between inspiration and expiration. Generally, the switching mechanism blocks the second gas channel 12 as soon as the ventilator switches to expiration. The switching can optionally take place with a time delay. Generally, the switching mechanism frees the second gas channel 12 when the ventilator switches to inspiration.

FIG. 1*b* furthermore shows the bypass channel 21. The bypass channel 21 extends from the opening and allows the gas stream flowing out of the opening to be guided past the non-return valve 19. The bypass channel 21 is formed peripherally about the opening and, in its further course, narrows to a channel which extends in a direction parallel to the first gas channel. The bypass channel 21 can then open again into the first gas channel or, as a separate branch, can carry away the gas stream that has been guided past the non-return valve.

In the region of the opening (not shown), the bypass channel has an edge on which the seal can be sealed by the closure cap 16. The edge of the bypass channel 21 can have an elevation behind which an edge of the seal can engage. The edge of the bypass channel 21 prevents slipping of the seal.

Figure 2:
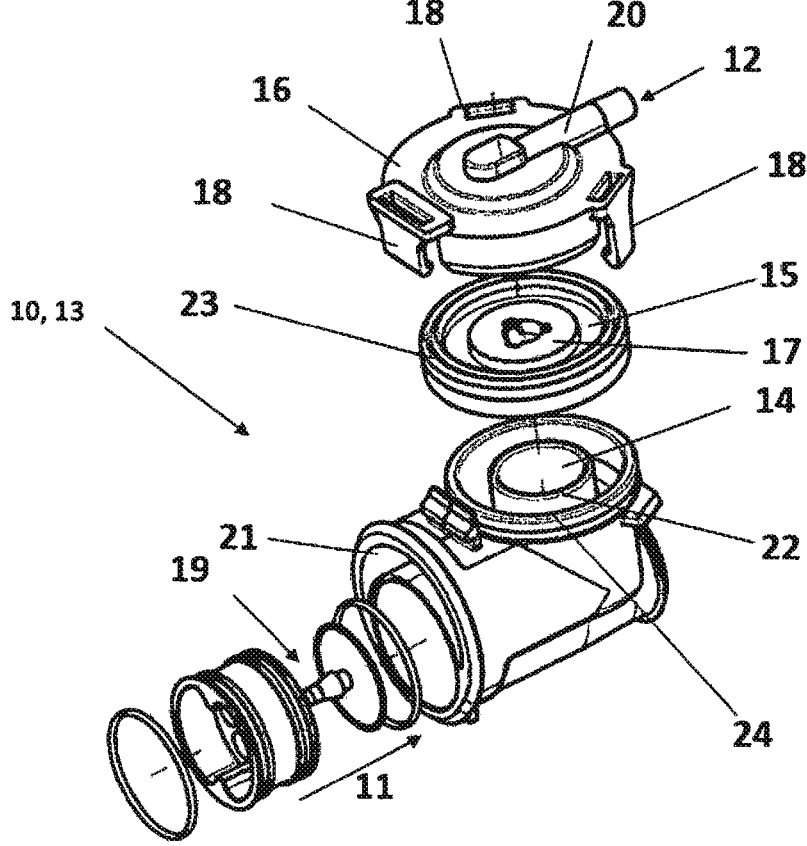
FIG. 2 shows a schematic exploded view of the gas control device shown in FIG. 1b.

FIG. 2 shows a schematic exploded view of the gas control device 10 shown in FIG. 1. The first gas channel 11 and second gas channel 12, the non-return valve 19 and the opening 14 with the seal 15 are shown here.

Also shown is the closure cap 16 with the connector piece 20. The central arrangement of the connector piece 20 is shown, wherein one end of the connector piece 20 extends outward and is connectable to the second gas channel 12.

FIG. 2 shows that the opening 14 has an edge 22. The edge 22 is designed as an elevation and serves as a support for the weight 17 integrated in the seal 15.

The seal 15 is made of an elastomeric material, preferably a silicone with a hardness of between 15 and 25 Shore A, in particular of between 18 and 22 Shore A. The seal 15 is circular and has a boundary 23.

The boundary 23 can be designed as a reinforced structure or as a functional elevation. The boundary 23 is configured to bear on an edge 24 of the bypass channel 21. The seal 15 can have a thinner material thickness between the boundary 23 of the seal 15 and the weight 17 than in the region of the edge 24 of the bypass channel 21 and the region of the seal 15 in which the weight 17 is arranged, mostly integrally.

In the present embodiment, the seal 15 has a curved structure between the edge 24 of the bypass channel 21 and the weight 17, said curved structure additionally being able to prevent displacement of the seal 15 on the opening 14. In further embodiments, the seal 15 can have a different structure or can be structure-free between the edge 24 of the bypass channel 21 and the weight 17.

The weight 17 of the seal 15 is in the form of a plain washer. The weight 17 is formed from a metal and is formed integrally in the seal 15. The weight 17 stabilizes the seal 15 on the opening 14.

When the closure cap 16 is placed onto the opening 14, the seal 15 is pressed, in the region of the boundary 23 of the seal 15, onto the edge of the bypass channel 21 and held. The closure cap 16 seals off the seal 15 to the outside and holds the seal 15 in its position inside the closure cap 16. The seal 15 is thus pressed on/held on the edge 24 of the bypass channel 21 inside the gas control device 10 by means of the clipped-on closure cap 16. The seal 15 is clamped/sealed between the edge 24 of the bypass channel 21 and the closure cap 16 via the peripheral, reinforced boundary 23.

Regions of the seal 15 that differ from the boundary 23 are formed in a contact-free manner with respect to the closure cap 16. These regions can also be referred to as charging regions, since the switching mechanism charges these regions of the seal 15 with a gas stream/pressure when the second gas channel 12 is freed.

In an inoperative state (without gas streams), the seal 15 is held by the weight and its structure on the opening 14. If the switching mechanism is configured to free the second gas channel 12, the charging regions of the seal 15 are additionally charged with a gas stream/pressure, as a result of which the seal 15 is sealed off on the opening 14.

If the switching mechanism is configured to block the second gas channel 12, the charging regions of the seal 15 are not charged with a gas stream, and therefore the gas stream of the first gas channel 11 is sufficient for lifting the seal in the region of the charging regions and for conducting the gas stream into the bypass channel 21.

The closure cap 16 shown in FIG. 2 comprises extensions 18 which form barbs. When the closure cap 16 is clipped on, the barbs engage in recesses which are formed on the outer side of the gas control device 10. In further embodiments, further closure options are conceivable, for example latching in the form of a bayonet catch. The non-return valve 19 and the bypass channel 21 are moreover shown in FIG. 2.

Figure 3:
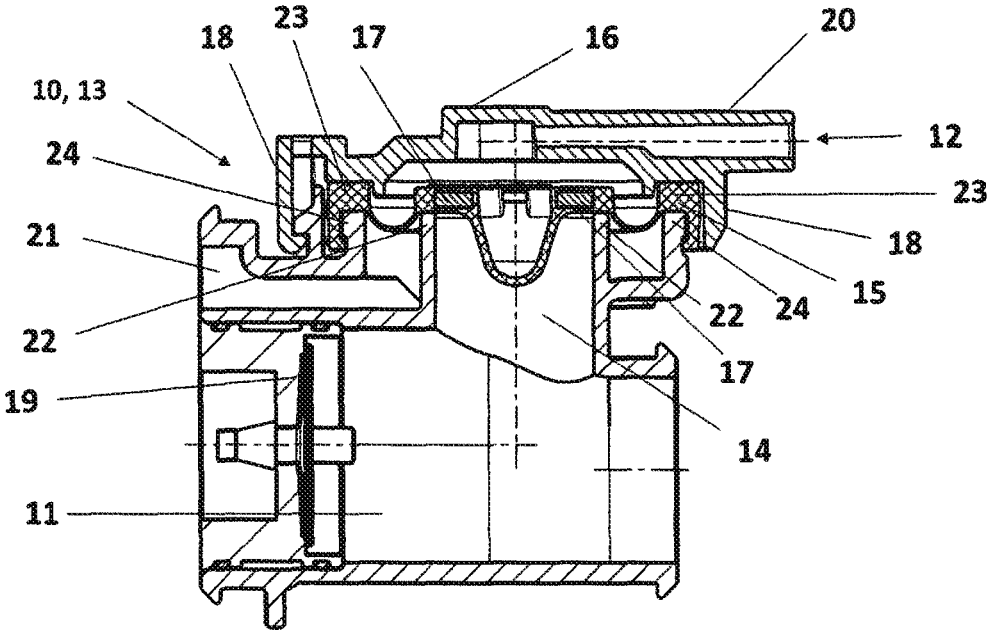
FIG. 3 shows a longitudinal section through the gas control device shown in FIGS. 1b and 2.

FIG. 3 shows a longitudinal section through the gas control device 10 shown in FIGS. 1 and 2. The first gas channel 11 with the non-return valve 19, the opening 14 and the seal 15 and also the second gas channel 12 are illustrated. In addition, the closure cap 16 with the connector piece 20 and the bypass channel 21 are illustrated.

An inspiratory gas stream can be conveyed to the patient via the first gas channel 11. The non-return valve 19 prevents exhaled gas from flowing back into the ventilator via the first gas channel 11. In the event of a blockage/disturbance of the expiratory branch of the ventilator, no expiration of the gas flow/exhaled gas can therefore take place via the first gas channel 11.

The bypass channel 21 which extends from the opening 14 is also shown. The bypass channel 21 is designed as an encircling channel around the opening 14 and extends in its further course to a channel which extends in a direction parallel to the first gas channel 11. By means of the encircling arrangement of the bypass channel, a large amount of exhaled gas can be simultaneously conducted around and past the non-return valve 19 and carried away via the opening 14. The bypass channel 21 can open into the inspiratory branch or can be designed as a separate expiratory branch.

The seal 15 is circular and has a weight 17 in its center. The weight 17 is ring-shaped/has the form of a plain washer. In its shape-induced cutout, the weight 17 has a conical configuration of the seal 15 that extends in the direction of the first gas channel 11. The conical configuration affords the advantage that the seal 15 is secured in its position on the opening 14 against slipping. In further embodiments, the configuration of the seal 15 can have a different geometrical shape which is suitable for holding the seal 15 in its position. The weight 17 is integrated in the seal 15. The seal 15 has a greater material thickness in the region of the weight 17. This firstly affords the advantage that the weight 17 can be integrated in the seal 15 and, secondly, the greater material thickness produces an additional weight 17 that holds the seal 15 in its position. The weight 17 can also be applied to the seal 15.

The closure cap 16 shown in FIG. 3 is arranged on the opening 14, wherein the closure cap 16, in the region of the boundary 23, presses the seal 15 onto the edge of the bypass channel 21, while the seal 15 is arranged in the charging regions in a contact-free manner with respect to the closure cap 16.

Figure 4A:
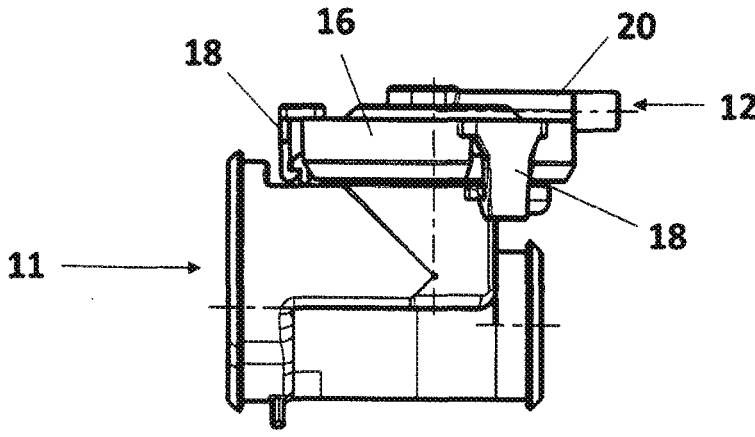
FIG. 4a shows a side view of the gas control device shown in FIGS. 1b to 3.

FIG. 4a shows a side view of the gas control device 10 shown in FIGS. 1 to 3. The first gas channel 11 and the closure cap 16 with the extensions 18 and the connector piece 20 for the second gas channel (not shown) are illustrated.

It can be seen in FIG. 4a that the inlet side of the first gas channel 11 is of a larger size than the outlet side. In addition to the first gas channel 11, the inlet side also comprises the bypass channel 21 which is narrowed to form a channel. The inlet side of the first gas channel 11 therefore comprises both the first gas channel 11, which is oriented in the inspiration flow direction, and the bypass channel 21, which is oriented counter to the inspiration flow direction.

Figure 4B:
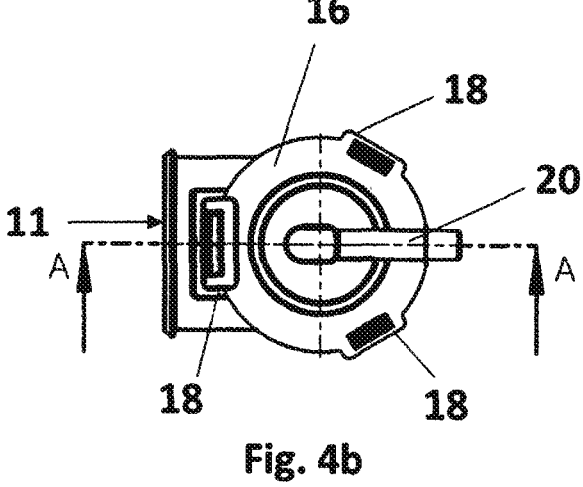
FIG. 4b shows a plan view of a closure cap, according to the invention, of the gas control device shown in FIGS. 1b to 4a, FIG. 4c shows a side view of a non-return valve of the gas control device shown in FIGS. 1b to 4b.

FIG. 4b shows a plan view of the closure cap 16, according to the invention, of the gas control device 10 according to the invention which is shown in FIGS. 1 to 4b. The closure cap 16 can be clipped onto the opening (not shown) of the first gas channel. When the closure cap 16 is clipped on, the seal, in the region of the weight (not shown) of the closure cap 16, is pressed onto an elevation 22 (shown in FIG. 3) of the opening and sealed.

The closure cap 16 has a connector piece 20 for the second gas channel 12 (not shown). The gas stream of the second gas channel 12 (not shown) can be applied to the seal (not shown) via the connector piece 20 in order to close the opening (not shown). The closure cap 16 furthermore comprises the extensions 18 which mostly form barbs and are configured to engage in recesses in the region of the opening. In further embodiments, the closure cap 16 can have further extensions 18 or can be secured on the opening via similar latching elements.

Figure 4C:
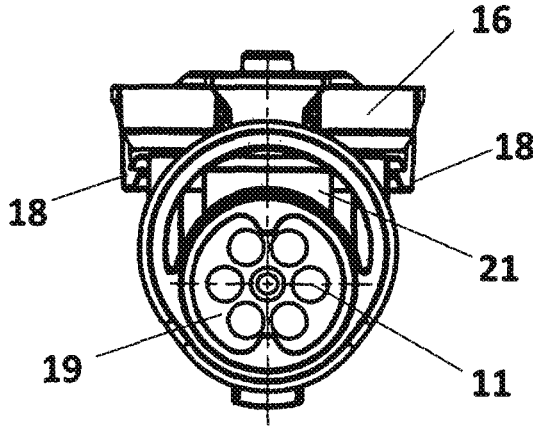

FIG. 4c shows a plan view of the non-return valve 19 of the gas control device 10 according to the invention shown in FIGS. 1 to 4b. The view here is of the non-return valve 19 from the direction of the inflowing gas stream, in the inspiration flow direction. Also shown is the bypass channel 21 via which the gas stream can be guided around the non-return valve 19 in the event of a blockage/disturbance of the expiratory branch of the ventilator.

The closure cap 16 is also illustrated in a side view, with the extensions 18 by means of which the closure cap 16 can be clipped onto the opening (not shown).

LIST OF REFERENCE NUMERALS 1 ventilator
10 gas control device
11 first gas channel
12 second gas channel
13 switching mechanism/valve block
14 opening
15 seal
16 closure cap of the opening
17 weight
18 extensions of the closure cap
19 non-return valve
20 connector piece
21 bypass channel
22 edge of the opening/elevation
23 boundary of the seal
24 edge of the bypass channel
25 gas stream, first direction
26 gas stream, second direction
27 breathing tube
28 tube port
29 environment
30 gas source, blower

What is claimed is:

1. A gas control device for a ventilator, wherein the device comprises a first gas channel with a first valve, the first gas channel and the first valve being configured to permit the passage of a pressurized gas stream being respiratory gas of inspiration in a first direction and to block a pressurized gas stream being respiratory gas of expiration in a second direction, an opening branching off from the first gas channel and leading to a bypass channel for the first valve, a second valve being configured to block and/or at least temporarily permit a gas stream from the first gas channel to the bypass channel, and a switching mechanism being configured to control the second valve to block and/or at least temporarily permit a gas stream from the first gas channel to the bypass channel, wherein the second the valve is configured as a pneumatic valve, a seal of the second valve closing or opening a gas-conveying connection between the opening and the bypass channel, wherein a second gas channel is configured to conduct a pneumatic control pressure onto a surface of the seal, the second gas channel being connected pneumatically to a breathing tube or the first gas channel or a blower, and the switching mechanism at least temporarily opening or closing the pneumatic connection and being configured such that if an expiratory branch of the ventilator is blocked or disrupted in a way that prevents or disrupts an exhalation of a patient, the second gas channel is blocked so that the blocked second gas channel causes the gas flow in the second gas channel, which acts on the seal, to come to a stop, as a result of which the gas flow in the first gas channel can lift the seal, which rests on the opening, so that the gas flow in the first gas channel is guided via the bypass channel around the first valve into the first gas channel and from there at least partially into the surroundings.

2. The gas control device of claim 1, wherein the first valve is a pneumatically actuated non-return valve, which is actuated by a force of the pressurized gas stream in the second direction, and therefore the gas stream cannot pass through the non-return valve in the second direction.

3. The gas control device of claim 1, wherein a respiratory gas source is configured to suction respiratory gas from the surroundings and to convey the suctioned respiratory gas along the first gas channel for inspiration in the first direction to a tube port and the breathing tube, the gas stream passing through the opened first valve which is a non-return valve.

4. The gas control device of claim 1, wherein the seal charged with the control pressure is configured to rest sealingly on an edge of the opening and thus prevent a gas stream from the opening into the bypass channel.

5. The gas control device of claim 1, wherein the seal the seal is made of an elastomeric material, is arranged to rest on the opening and comprises a weight made of metal that is present as a ring in a center of the seal.

6. The gas control device of claim 1, wherein the seal comprises an embossing, which is formed in the region of the weight, facing in a direction of the first gas channel.

7. The gas control device of claim 1, wherein the first gas channel comprises the opening for an outflow of gas with the seal and a closure cap.

8. The gas control device of claim 7, wherein the closure cap is configured to be placeable onto the opening, and comprises a connector piece, which is connectable to the second gas channel.

9. The gas control device of claim 8, wherein, during normal operation of an expiratory branch, the switching mechanism is configured to free the second gas channel and to convey a gas stream/pressure via the second gas channel and the connector piece to the seal and close the opening.

10. A ventilator, wherein the ventilator comprises the gas control device of claim 1.

* * * * *